United States Patent
Bao et al.

(10) Patent No.: US 10,883,947 B2
(45) Date of Patent: Jan. 5, 2021

(54) SORBENT BASED GAS CONCENTRATION MONITOR

(71) Applicant: Palo Alto Research Center Incorporated, Palo Alto, CA (US)

(72) Inventors: Jianer Bao, Sunnyvale, CA (US); Clinton Smith, San Francisco, CA (US); Eric Cocker, Redwood City, CA (US); David Schwartz, Concord, MA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 372 days.

(21) Appl. No.: 15/800,788

(22) Filed: Nov. 1, 2017

(65) Prior Publication Data

US 2019/0128827 A1    May 2, 2019

(51) Int. Cl.
*G01N 25/48* (2006.01)
*G01N 33/00* (2006.01)
(Continued)

(52) U.S. Cl.
CPC ....... *G01N 25/482* (2013.01); *G01N 25/4826* (2013.01); *G01N 25/4873* (2013.01);
(Continued)

(58) Field of Classification Search
CPC ............. G01N 25/482; G01N 25/4893; G01N 25/4873; G01N 25/4826; G01N 33/004; G01K 3/14; G01K 7/22; G01K 2213/00
See application file for complete search history.

(56) References Cited

U.S. PATENT DOCUMENTS

| 6,500,238 B1 * | 12/2002 | Brandes ................. | B01D 53/04 95/148 |
| 7,338,640 B2 * | 3/2008 | Murthy .............. | G01N 25/4893 374/10 |

(Continued)

FOREIGN PATENT DOCUMENTS

| JP | 20110033592 A | 2/2011 |
| WO | 20170145889 A1 | 8/2017 |

OTHER PUBLICATIONS

International Search Report for International Application No. 18203231.8, dated Jun. 27, 2019.
(Continued)

*Primary Examiner* — Jonathan M Dunlap
(74) *Attorney, Agent, or Firm* — Womble Bond Dickinson (US) LLP

(57) ABSTRACT

A gas monitor apparatus includes a sorbent material that adsorbs a target gas based on a concentration of the target gas in a monitored environment and a reference material that does not respond to the target gas. The gas monitor also includes a first thermistor disposed within the sorbent material and a second thermistor disposed within the reference material, the first thermistor to provide a first indication of a first temperature of the sorbent material and the second thermistor to provide a second indication of a second temperature of the reference material. A processing device determines a concentration of the target gas based at least in part on a differential measurement between the first temperature and the second temperature.

18 Claims, 9 Drawing Sheets

(51) Int. Cl.
*G01K 7/22* (2006.01)
*G01K 3/14* (2006.01)

(52) U.S. Cl.
CPC ....... *G01N 25/4893* (2013.01); *G01N 33/004* (2013.01); *G01K 3/14* (2013.01); *G01K 7/22* (2013.01); *G01K 2213/00* (2013.01)

(56) References Cited

U.S. PATENT DOCUMENTS

| | | | | |
|---|---|---|---|---|
| 9,261,472 | B2* | 2/2016 | Kimura | G01N 25/4826 |
| 9,370,749 | B2* | 6/2016 | Addleman | C09D 183/04 |
| 9,457,340 | B2* | 10/2016 | Buelow | B01J 20/3236 |
| 10,466,190 | B1* | 11/2019 | Ancona | G01N 1/405 |
| 2001/0041366 | A1* | 11/2001 | Lewis | A61B 5/00 |
| | | | | 436/151 |
| 2003/0033930 | A1* | 2/2003 | Tom | B01D 53/0407 |
| | | | | 95/45 |
| 2004/0112117 | A1 | 6/2004 | Wright | |
| 2006/0220164 | A1* | 10/2006 | Murthy | G01N 25/4893 |
| | | | | 257/467 |
| 2008/0051279 | A1* | 2/2008 | Klett | B01J 20/183 |
| | | | | 502/60 |
| 2008/0056946 | A1* | 3/2008 | Ahmad | G01N 33/50 |
| | | | | 422/68.1 |
| 2009/0074612 | A1* | 3/2009 | Gross | G01N 7/02 |
| | | | | 422/400 |
| 2009/0288962 | A1* | 11/2009 | Yantasee | G01N 27/42 |
| | | | | 205/790 |
| 2010/0116024 | A1* | 5/2010 | De Coulon | G01N 27/18 |
| | | | | 73/25.03 |
| 2013/0095996 | A1* | 4/2013 | Buelow | B01J 20/3236 |
| | | | | 502/62 |
| 2013/0209315 | A1* | 8/2013 | Kimura | G01N 25/4826 |
| | | | | 422/88 |
| 2014/0092935 | A1* | 4/2014 | Lin | G01N 25/48 |
| | | | | 374/10 |
| 2015/0367035 | A1* | 12/2015 | Kumaraswamy | A61L 27/446 |
| | | | | 435/396 |
| 2016/0103082 | A1* | 4/2016 | Kimura | G01N 33/005 |
| | | | | 73/25.01 |
| 2016/0216163 | A1* | 7/2016 | Lin | G01N 25/4893 |
| 2016/0334330 | A1* | 11/2016 | Kobayashi | G01N 21/3504 |
| 2017/0072493 | A1* | 3/2017 | Kobayashi | G01N 21/3504 |
| 2017/0307553 | A1* | 10/2017 | Jia | G01K 17/006 |
| 2017/0341351 | A1* | 11/2017 | Iwasaki | B32B 27/36 |
| 2019/0049398 | A1 | 2/2019 | Nojiri | |

OTHER PUBLICATIONS

Hornbostel et al. "Characteristics of an advanced carbon sorbent for $CO_2$ capture"; Carbon 56 (2013) pp. 77-85.

* cited by examiner

SORBENT BASED GAS CONCENTRATION MONITOR

TECHNICAL FIELD

Implementations of the present disclosure relate to measurement of gasses present in a system.

BACKGROUND

Gasses present in a system of atmosphere may affect people or the performance of components present in the area. Measurement of gasses may be performed with a number of techniques based on properties of the gas and the concentration of the gas present.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

Figure 1:
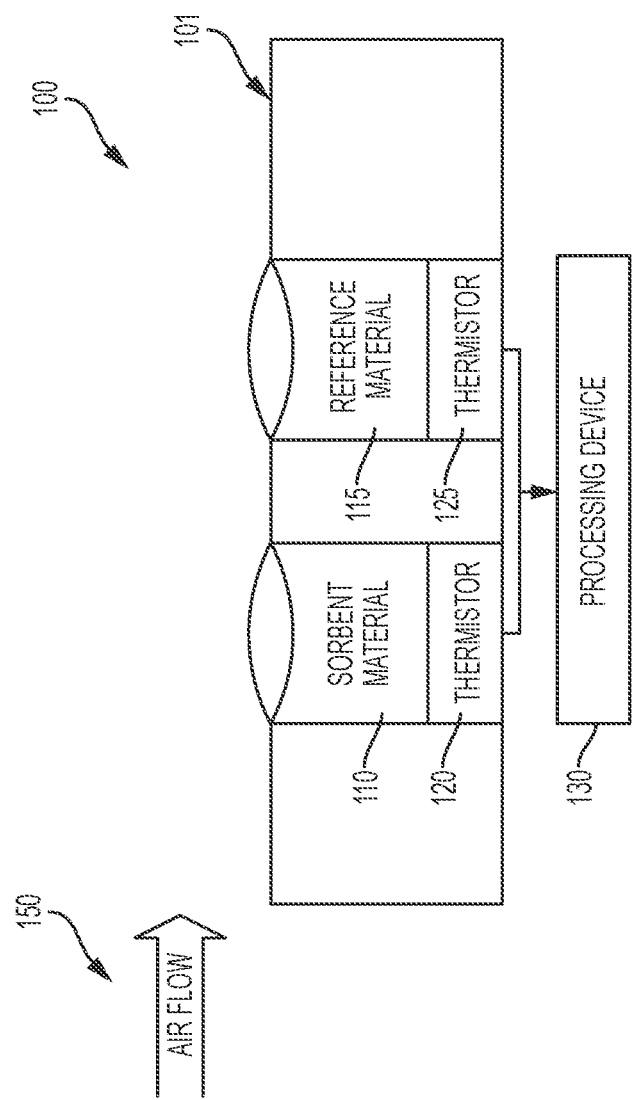
FIG. 1 is a schematic diagram of an embodiment of a gas monitor, which can be used in accordance with some embodiments.

Measurement of gas levels within different environments is important to ensure quality of air, lack of pollutants, quality control in manufacturing, and a number of different reasons. However, some gas level monitoring solutions may be expensive, large, require high power consumption, or have other drawbacks that prevent widespread use within different environments. In addition, with increasing connection between various consumer devices, opportunities for remote sensing of various home parameters exist. For example Internet of Things connected devices may be dispersed through a home or facility and provide information to one another, to a central server, or to a local control device. Large, expensive, or high power consuming gas monitors may not be practical for implementation in a connected facility. Accordingly, smaller, cheaper, and low power consumption gas monitoring systems may enable wider utilization of such measurement systems.

In some embodiments, a gas monitor monitors the temperature of a sorbent material to determine changes to the concentration of a gas within a system. For example, if the concentration of a gas in a monitored environment is increased, the sorbent material may adsorb more of the gas. Then, as the gas is adsorbed by the sorbent material, the temperature of the sorbent may increase. Thus, the gas monitor determines a concentration of the gas, or a change in the concentration of the gas, based on monitoring the temperature of the sorbent material.

In some embodiments, a gas monitor may include a reference material in addition to the sorbent material. The reference material may act as a control to compare with the gas monitor. The gas monitor may determine a differential measurement between the sorbent material and the reference material. The differential measurement may provide an indication of the change in the temperature of the sorbent material compared to changes in the environment due to other causes. For example, due to changes in air temperature of the monitored environment.

In some embodiments, the gas monitor may passively measure changes to the differential temperature of the sorbent material and reference material. If the concentration of a target gas increases, then the sorbent material may adsorb more of the gas and increase temperature. Thus, the differential measurement may increase, indicating that the temperature of the sorbent material increased. If the concentration of the target gas decreases, then the sorbent material may release the target gas back to the atmosphere and decrease in temperature. Thus, the differential measurement may also decrease, indicating that the temperature of the sorbent material decreased. Based on the changes in the differential temperature measurement, the gas monitor may determine if the concentration of the target gas changes. The gas monitor may provide an indication or report of any change of the concentration of the target gas to a monitoring or alarm system.

Measuring the differential temperature of the sorbent material and the reference material may provide an indication of the changes to the concentration of the target gas. However, in some situations, it may be beneficial for the gas monitor to determine an absolute value for the concentration of the gas in the monitored environment. Therefore, in some embodiments, the temperature of the sorbent material and reference material may be controlled to monitor absolute characteristics of the environment. For example, by raising and lowering the temperature of the sorbent material, the sorbent material may respectively adsorb and release a target gas. Furthermore, in some embodiments, a gas monitor may calibrate the system by heating the system to desorb all of the target gas from the sorbent. Adsorbing and releasing the target gas may affect the rate of temperature change of the sorbent material compared to the reference material. The gas monitor may determine a differential temperature measurement between the sorbent material and the reference material based on the difference in the rate of change of the temperature of the sorbent material. The change in the rate of change of the temperature of the sorbent material is based on the concentration of the target gas in the monitored environment. Accordingly, the gas monitor may determine an absolute measurement for concentration of the target gas in the monitored environment based on the differential measurement as the temperature of the sorbent material and the reference material are raised and lowered by the gas monitor.

In order to provide an accurate measurement of changing concentrations of a target gas or absolute concentrations of a target gas, appropriate sorbent materials and reference materials may be selected. In some embodiments, the sorbent material may be reasonably selective to a particular target gas or class of target gasses. For example, the sorbent may only adsorb a particular gas or a set of gasses that are part of a family of related gasses. A sorbent may also be placed within a system having filters or getters to improve selectivity. For example, filters and getters may prevent the sorbent from adsorbing gasses other than the target gas. This may increase the relative selectivity of the sorbent for the target gas. In some embodiments, the sorbent material may also have a high thermal conductivity so that heat is transferred to a thermistor or other temperature measurement device. In some embodiments, the high thermal conductivity may also provide better temperature control by a heat source. The sorbent material may also have a high surface area, or may be a porous structure, in order to improve the amount of target gas loading on the sorbent. Additionally, the sorbent material may have an intermediate binding energy. For example, the intermediate binding energy may provide a reversible interaction with the target gas (i.e., adsorption and desorption). The reversible interactions may provide the gas monitor with the ability to monitor the absolute concentration of the target gas over time.

In addition to the sorbent material, a reference material may be selected that has similar thermal properties to the sorbent material. Having similar thermal properties may provide an accurate differential measurement between the reference material and the sorbent material. For example, if the reference material had lower thermal conductivity, a differential measurement may be formed based on the difference between the rates of change to an ambient temperature of the environment and reduce the accuracy of the gas monitor.

The gas monitors described herein may be utilized for any gas measurement that has a sorbent material suitably selected to adsorb and release a target gas and generate a reasonable heat of adsorption. For example, in some embodiments, the gas monitor may selectively adsorb $CO_2$. $CO_2$ monitoring may be important for maintaining healthy indoor air quality. Additionally, there are various regulations indicating $CO_2$ levels that are appropriate for occupied indoor spaces. While various techniques may be applied to generate ventilation requirements to meet standards and regulations, without measuring $CO_2$ levels in particular rooms of a building, some parts of the building may be over ventilated or under ventilated. Accordingly, $CO_2$ levels may not meet standards in all areas, or excessive energy may be expended to over ventilate some areas. To improve air quality and energy costs, deploying multiple $CO_2$ monitors as described herein may give additional insight into the actual $CO_2$ levels of rooms. As an example, ASHRAE Standard 62.1-2016 indicates that concentrations of $CO_2$ in an indoor space should be kept below 700 ppm above outdoor air concentration levels. It is suggested that approximately 7.5 L/s/person of ventilation is required, but this is not a direct indication of the actual concentration of $CO_2$ in indoor air. The actual ventilation required to achieve the standard could be based on activity level and other features of a particular indoor space. Thus, by reducing the size and power consumption of devices to enable more widespread deployment of $CO_2$ sensors as described herein, better air quality may be achieved at a lower energy consumption.

In some embodiments, an appropriate binder may effectively improve the thermal conductivity of the sorbent material and the reference material. Notably, with a high surface area porous sorbent, a large molecular size (for example, greater than 0.1 µm) binder may reduce the chance that sorbent particles are filled with the binder. In some embodiments, a carbon sorbent may be used for detection of $CO_2$. For example, Entegris BrightBlack® may be used as a sorbent. In some embodiments, other carbon sorbents may be used instead of Entegris BrightBlack®. For example, another microporous and nanoporous carbon material may be used. In some embodiments, other high surface materials with medium binding energy surface groups may be used. For example, the sorbent may be a metal-organic-framework, a zeolite, carbon nanotubes, graphenes, silanized aerogels, or a combination of such materials. In an example binder related to a carbon sorbent of $CO_2$ gas, a styrene acrylic-based polymer latex with a molecular size of about 0.1-0.15 µm or porous glassy solid binder from colloidal silica may provide a suitable structure. In some embodiments, a carbon sorbent used in the sorbent material may act as a molecular sieve, with pore size below a few nanometers. Thus, pore filling may be limited with a number of binders. However, surface blocking still needs to be minimized to enhance the kinetics of the target gas adsorption into the sorbent material. Accordingly, dispersion of the carbon sorbent particles and a homogeneous distribution of particles and binders may improve thermal conductivity with minimal amount of binders. In some embodiments, binders and sorbents may be dry mixed to enhance thermal conductivity.

In some embodiments, thermal conductivity between the sorbent material and the thermistor may be improved by maximizing the contact surface area between a thermistor and the printed sorbent material. The thin printed sorbent bed may be used so that both sorbent material heat conduction and sorbent/thermistor interface heat conduction can be improved. In some embodiments, calendaring with a mild pressure may also be used to further enhance the thermal conductivity.

The configurations discussed below are generally described as having a single sorbent material. In some embodiments, a gas monitor may have more than one sorbent material. For example, more than one sorbent material may be placed at different positions on a substrate to provide additional accuracy. Furthermore, in some embodiments the gas monitor may have more than one sorbent material of different types. For example, a first sorbent material may target a first gas and a second sorbent material may target a second gas. The gas monitor can then monitor the concentration of multiple gasses. In some embodiments with multiple sorbent materials, there may be a single reference material portion that is used as a control for each of the sorbent materials. For example, one or more reference materials may be a carbon nanotube based structure. The reference material may be the same or similar type of material as described with reference to the sorbent materials above, for instance. In some embodiments, there may be additional reference materials that are used to act as controls for one or more other sorbent materials. In some embodiments, the reference material may be the same material as the sorbent material, but that hasn't been activated, or may be encapsulated such that it does not interact with the monitored environment.

Other gas monitors may use different sorbents materials to target other gasses. For example, other sorbents may be reasonably selective through both thermal modulation and surface treatments to change the functional groups of the previously mentioned sorbent materials to adsorb carbon monoxide, Benzene, formaldehyde, or other biologically reactive gasses. As an example, Benzene may be monitored in a manufacturing setting to ensure a safe work environment and proper functioning of machinery. For example, Benzene may be selectively adsorbed using this kind of approach. As another example, Formaldehyde may be monitored to determine if a person has been smoking in a room.

In addition to measuring air quality and presence of gasses in indoor spaces, gas monitors based on the temperature change of sorbents may be used to monitor the air quality in cars, submarines, boats, outdoor spaces such as stadiums, inside manufacturing facilities or machines, or the like. In some embodiments, the gas monitors as described herein may be used to monitor a target gas for other relevant environments.

FIG. 1 is a diagram showing an example embodiment of a gas monitor 100. The gas monitor includes a sorbent material 110 and a reference material 115. The temperature of sorbent material 110 and reference material 115 may be measured by respective thermistors 120, 125. In some embodiments, the gas monitor 100 may have other temperature measurement devices. A processing device 130 may receive signals from thermistors 120, 125 and based on a difference between the temperature measurements, may make a determination of the concentration of a target gas within air flow 150.

In some embodiments, the sorbent material 110 may be a sorbent printed on a substrate 101 that selectively adsorbs a target gas. In some embodiments, the sorbent material may have been combined with a binder and solvent, then printed to produce a porous structure with high surface area to mass ratio. The high surface area may increase the effect of adsorption on the temperature of the sorbent material 110. In some embodiments, the sorbent material may be a powder, solid core, or other structure rather than a printed sorbent.

The reference material 115 may be similar structurally to the sorbent material 110. For example, the reference material 115 may be printed on a substrate 101 in a same or similar manner as the sorbent material 110. For example, the reference material 115 may be printed using a similar binder and solvent that was used to print the sorbent material 110. Furthermore, if the sorbent material 110 has other structures, the reference material 115 may have a similar structure or manufacturing process. In some embodiments, the reference material 115 may have similar thermal properties as the sorbent material 110. For example, the reference material 115 may have similar size, weight, thermal conductivity, and other properties as the sorbent material 110. However, compared to the sorbent material 110, the reference material 115 may not be responsive to the target gas or other gasses that are likely to be present in air flow 150. In some embodiments, reference material 115 may behave similarly to the sorbent material 110 in response to gasses other than the target gas. In some embodiments, the reference material 115 may include polymer beads or metal/oxide particles.

In some embodiments, thermistor 120 and thermistor 125 may be similar components. For example, the thermistors 120, 125 may have the same or similar structure. In some embodiments, thermistor 120 and thermistor 125 may have different structures. Furthermore, while discussed as thermistors, in some embodiments, the thermistors may be replaced with other temperature sensing devices. In some embodiments, thermistors 120, 125 may be disposed within the sorbent material 110 and reference material 115. For example, the thermistors 120 may extend within the sorbent material 110 to increase the accuracy or speed of temperature measurements. The thermistors 120, 125 may be electronically coupled to a processing device 130. For example, thermistors 120, 125 may provide an indication of temperature of the sorbent material 110 and reference material 115.

The processing device 130 may receive signals from thermistors 120, 125 that indicate the temperature of the sorbent material 115 and reference material 110. The processing device may include one or more processors such as a microprocessor, central processing unit, or the like. In some embodiments the processing device 130 may be an application specific integrated circuit (ASIC), a field programmable gate array (FPGA), a digital signal processor (DSP), network processor, or the like. Furthermore, the processing device may include one or more memory devices such as a main memory, random access memory, or other computer readable storage mediums.

In some embodiments, the thermistors 120, 125 may be electronically coupled to the processing device 130 in a manner to provide a differential measurement of temperature of the sorbent material 110 and the reference material 115. In some embodiments, the processing device 130 may determine a temperature difference between the sorbent material 110 and the reference material 115 based on different indications of temperature from the thermistors 120, 125. In some embodiments, the processing device may use the temperature differential to determine a change in the concentration of a target gas. For example, the processing device 130 may determine that the concentration of the target gas has increased in view of a higher temperature indication from thermistor 120 compared to the temperature indication from thermistor 125. Furthermore, the processing device 130 may determine that the concentration of the target gas has decreased in view of a lower temperature indication from the thermistor 120 compared to the temperature indication from the thermistor 125.

In some embodiments, the processing device 130 may provide a signal of changes to the concentration of the target gas to another system. For example, the processing device 130 may provide an indication to a control system, an alarm system, or another system of changes to the concentration of the target gas. In some embodiments, the processing device 130 may be a remote system to the sorbent material 110 and reference material 115. For example, thermistors 120, 125 may provide indications of temperature of the sorbent material 110 and reference material 115 through a wired or wireless electronic connection to the processing device 130 at a remote location.

In some embodiments, the processing device 130 may determine a change in the concentration of the target gas based on the determined temperature differential between the sorbent material 110 and the reference material 115. However, as discussed above, in some embodiments, a gas monitor may determine the absolute concentration of the target gas in air flow 150.

Figure 2:
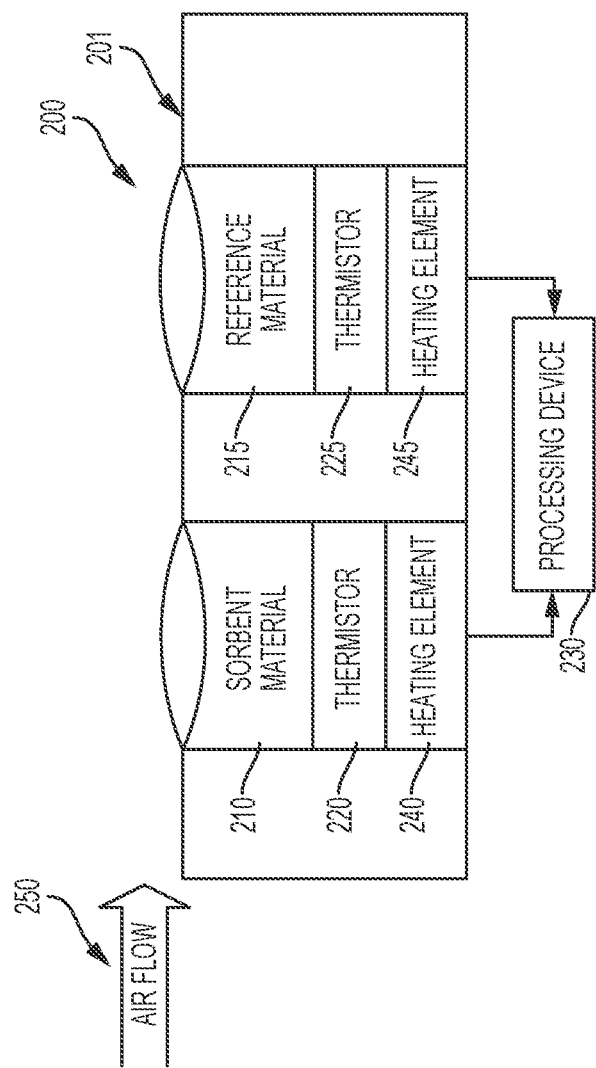
FIG. 2 is a schematic diagram of an embodiment of a gas monitor, which can be used in accordance with some embodiments.

FIG. 2 is a diagram showing an example embodiment of a gas monitor 200. The gas monitor 200 may be similar to the gas monitor 100 described with reference to FIG. 1. For example, the gas monitor 200 may include a sorbent material 210 with associated thermistor 220, and a reference material 215 with associated thermistor 225. Thermistors 220, 225 may be electrically coupled to processing device 230 to provide an indication of the temperature of the sorbent material 210 and reference material 215.

In addition to the described portions of gas monitor 200 that are similar to those of gas monitor 100, the gas monitor 200 may include heating elements 240, 245. The heating element 240 may be operatively coupled to the sorbent material 210. Thus, the heating element 240 may provide heat to the sorbent material 210 and the heating element 245 may provide heat to the reference material 215. In some embodiments, the heating element 240 and the heating element 245 may be combined as a single heating element. Furthermore, in some embodiments, the thermistor 220 and heating element 240 may be the same element and the thermistor 225 and the heating element 245 may be the same element. For example, the thermistor 220 may both change resistance to provide an indication of temperature and be used as a heating element by providing current across the thermistor 220. The thermistor 225 may be used in a similar manner to provide heat to the reference material. In some embodiments, heating elements 240, 245 may be resistive heating elements that provide heat to the sorbent material 210 and the reference material 215 in response to a current across the heating elements.

The processing device 230 may be coupled to the heating element 240 and heating element 245 to control the heating elements. In some embodiments, the processing device 230 may provide current across the heating elements 210, 215 in a periodic manner to raise and lower the temperature of the sorbent material 210 and reference material 215. The sorbent material 210 and reference material 215 may then change temperature in response to the provided heat. The reference material 210 may increase and decrease temperature at a different rate than the sorbent material 210. For example, the sorbent material 210 may increase and decrease temperature due to the change in heat provided from heating element 240, but may also adsorb and release the target gas based on the change in temperature. Accordingly, the thermistor 220 associated with the sorbent material 210 and the thermistor 225 associated with the reference material 215 may provide a differential indication of temperature of the sorbent material 210 and reference material 215. In some embodiments, the gas monitor 200 may determine an amount of current used to heat a sorbent to a reference temperature. The amount of current used may indicate the amount of the target gas on the sorbent 210. Accordingly, the processing device 230 may determine a concentration of the target gas in the environment based on the amount of current used.

Based on the differential temperature measurements provided by the thermistors 220, 225, the processing device 230 may determine an absolute concentration of the target gas in air flow 250. For example, the processing device may compare the temperature indications from the thermistor 225 and 220 to a set of calibrated values for the temperature of the sorbent material 210 at particular temperatures and concentrations of the target gas to determine an absolute measurement of the concentration of the target gas.

While the components of gas monitor 200 have been shown in a particular configuration, in other embodiments, the components may be configured differently in different embodiments. For example, while shown in three layers, in some embodiments, the thermistors 220, 225, sorbent material 210, reference material 215, and heating elements 240, 245 may be configured differently. Furthermore, the positions of the sorbent material 210 with respect to the reference material 215 may be different. In some embodiments, the thermistors 220, 225 and heating elements 240, 245 may be on opposite sides of the sorbent material 210 and reference material 215. Furthermore, in some embodiments, the thermistors 220, 225, sorbent material 210, reference material 215, and heating elements 240, 245 may be coplanar. For example, the heating element 240 may be on one side of a sorbent material 210 and the thermistor 220 may be on the other side in a printed plane. In some embodiments, other configurations may be used, for example, components of the gas monitor 200 may be arranged in a concentric configuration, stacked configuration, in any number of layers, or in other configurations wherein the components of the gas monitor operate as described with reference to the gas monitor 200.

Figure 3A:
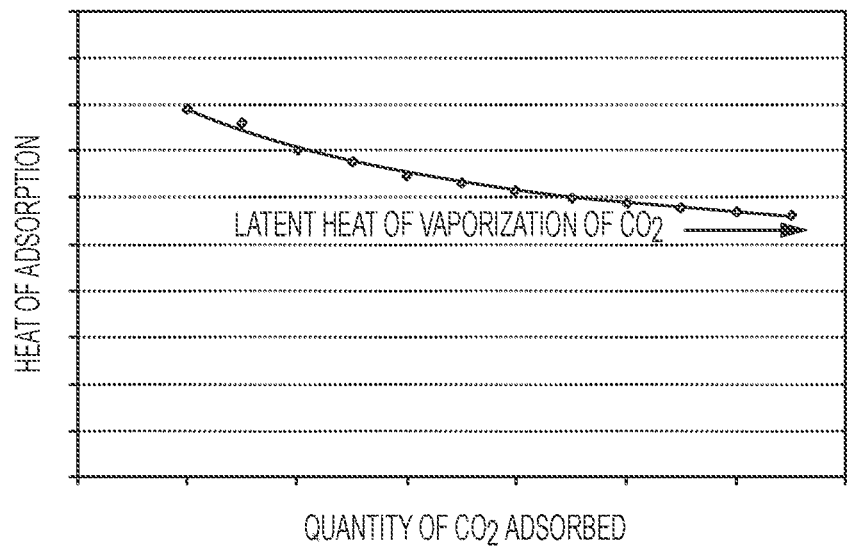
FIG. 3A is a graph showing an example relationship between the quantity of a target gas adsorbed by a sorbent and the change in the heat of adsorption for the system.
Figure 3B:
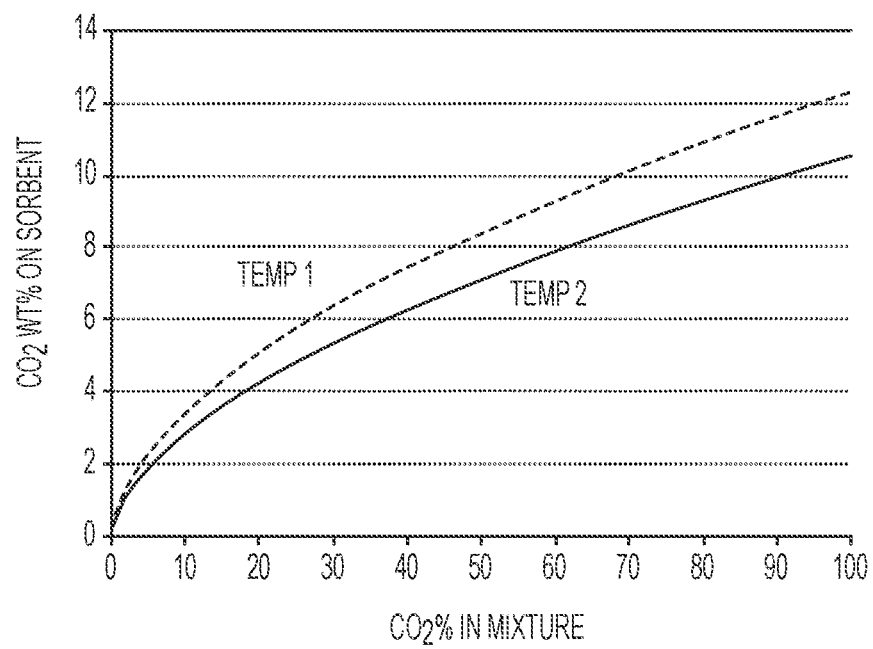
FIG. 3B is a graph showing an example relationship between the concentration of the target gas in the monitored environment and the amount of the target gas on a carbon sorbent.

FIGS. 3A and 3B depict graphs showing the relationship of characteristics of an example carbon based sorbent to the adsorption of $CO_2$ by the sorbent. FIG. 3A shows the relationship between the quantity of $CO_2$ adsorbed by a sorbent and the change in the heat of adsorption for the system. As shown in FIG. 3A, as the sorbent absorbs more $CO_2$, the heat of adsorption in the sorbent material approaches the latent heat of vaporization of $CO_2$ in the environment. FIG. 3B shows the relationship between the concentration of the $CO_2$ in the monitored environment and the amount of $CO_2$ on a carbon sorbent. The graph includes a first curve showing the relationship at 20° C. and a second curve showing the relationship at 30° C. As shown in the graph, at a lower ambient temperature (the 20° C. curve), the amount of $CO_2$ on the carbon sorbent is higher for a given $CO_2$ concentration in the air.

Figure 4:
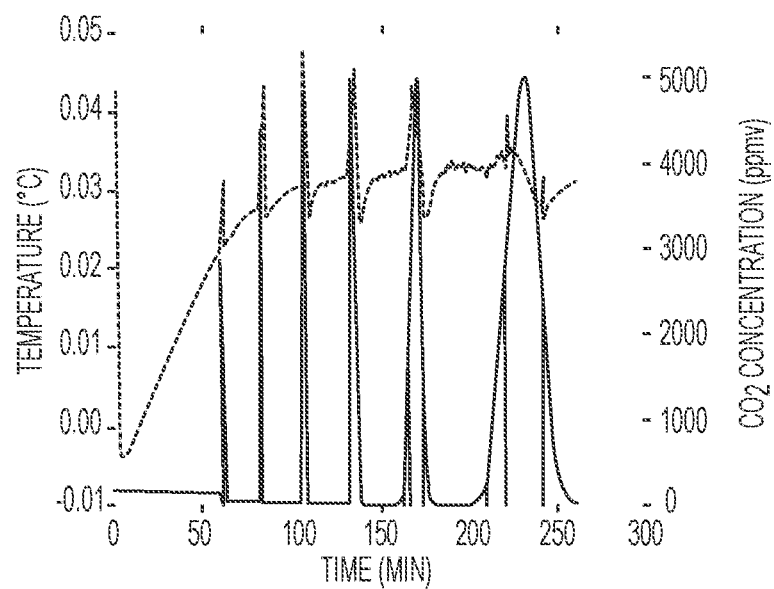
FIG. 4 is a graph showing an example of a differential temperature response of a sorbent material and reference material when exposed to changing $CO_2$ concentrations.
Figure 5:
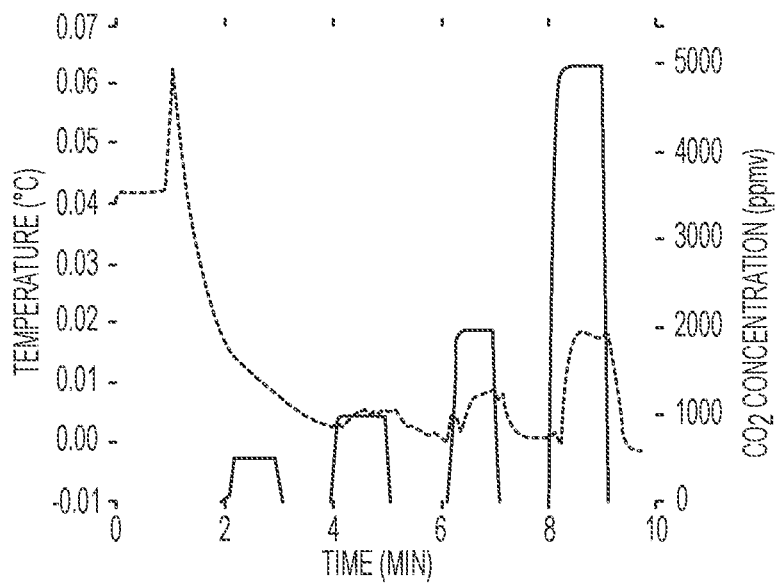
FIG. 5 is a graph showing an example of a differential temperature response of a sorbent material and reference material when exposed to changing $CO_2$ concentrations, according to an embodiment.

FIG. 4 is a graph showing a differential temperature response of a sorbent material and reference material when exposed to changing $CO_2$ concentrations, according to an embodiment. FIG. 5 is a graph showing a differential temperature response of a sorbent material and reference material when exposed to changing $CO_2$ concentrations, according to an embodiment. FIG. 5 shows the response to changing $CO_2$ concentrations at a different time scale. As can be seen in both FIG. 4 and FIG. 5, as the $CO_2$ concentration is increased in the environment that a gas monitor is exposed to, the temperature differential between the sorbent material and reference material correspondingly changes. Notably, as $CO_2$ is exposed to the gas monitor, the temperature differential is increased and as $CO_2$ is removed from the environment, the temperature differential is decreased.

Because the sorbent temperature only provides an indication of the heat of adsorption, it acts as a derivative operation and cannot alone quantify the absolute $CO_2$ concentration. This effect can be seen in FIGS. 4 and 5, in which the thermistor response appears as a derivative of the $CO_2$ concentration. In order to determine the absolute concentration of $CO_2$, a gas monitor may integrate the thermistor differential output over time.

In some embodiments, the differential temperature indications may be integrated to determine aggregate changes over time. The differential temperature indications may be integrated using a processing device or integrating circuit. In some embodiments, the differential temperature indications may be integrated in combination with using a modified 4-wire resistance measurement scheme. For example, a Wheatstone bridge configuration may be used to reduce the effects of noise and drift to generate an integrated signal.

Figure 6:
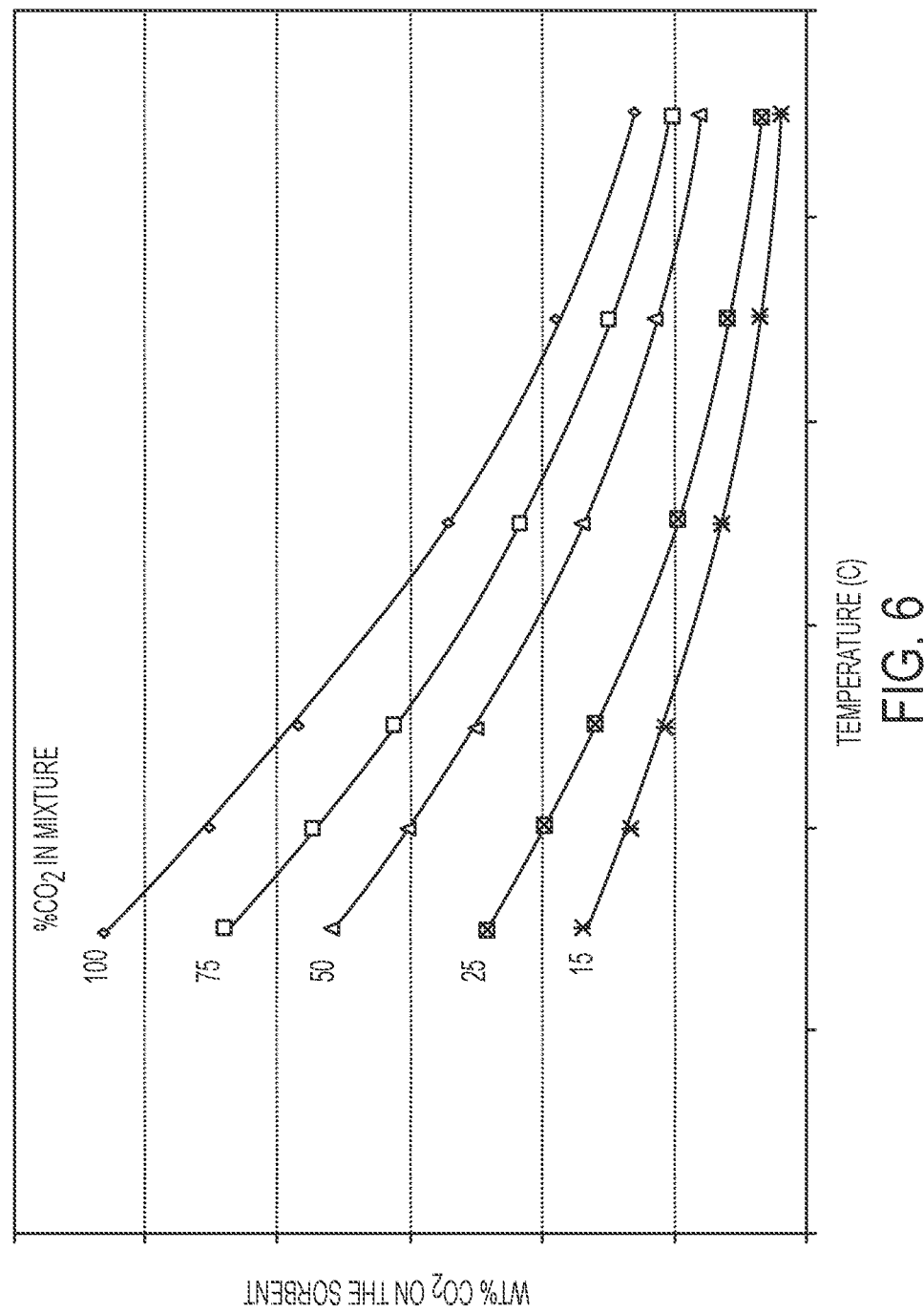
FIG. 6 is a graph showing an example of adsorptive loading on a sorbent as a function of temperature and gas concentration.

FIG. 6 is a graph showing adsorption loading of $CO_2$ gas on a sorbent as a function of temperature and gas concentration. The graph shows changing in temperature based on increasing and decreasing the concentration of $CO_2$ at different temperatures. As shown in FIG. 2, a gas monitor may change the temperature of a sorbent material and reference material to effect the adsorption and release of $CO_2$ from the sorbent material.

In some embodiments, based on the known measurements of a target gas and a sorbent temperature change as described with reference to FIG. 6, a processing device may apply a probe current to create a voltage across the target resistor to apply a heat source to a sorbent material and reference material. In some embodiments, a separate circuit may employ a high impedance amplifier to measure the voltage. In some embodiments, the probe current may simultaneously heat the sorbent in order to volatilize adsorbed target gasses. For example, the processing device may modulate a probe current in order to alternatively heat and cool the sorbent and to create a periodic signal that will enable absolute $CO_2$ concentration measurement. Absolute $CO_2$ concentration quantification by modulation of the sorbent temperature is possible because the $CO_2$ has a relatively fixed vapor pressure and heat of adsorption. Modulation of the sorbent temperature correspondingly shifts a Langmuir Isotherm curve associated with the sorbent and target gas. This may cause the sorbent to alternatively adsorb or release the target gas. Thus, the sorbent material may be moved along the x-axis of FIG. 6. The concentration of $CO_2$ dictates which curve in FIG. 6 is sampled. The resulting thermal response of the sorbent from the adsorption/desorption can be measured via the thermistor circuit.

Figure 7:
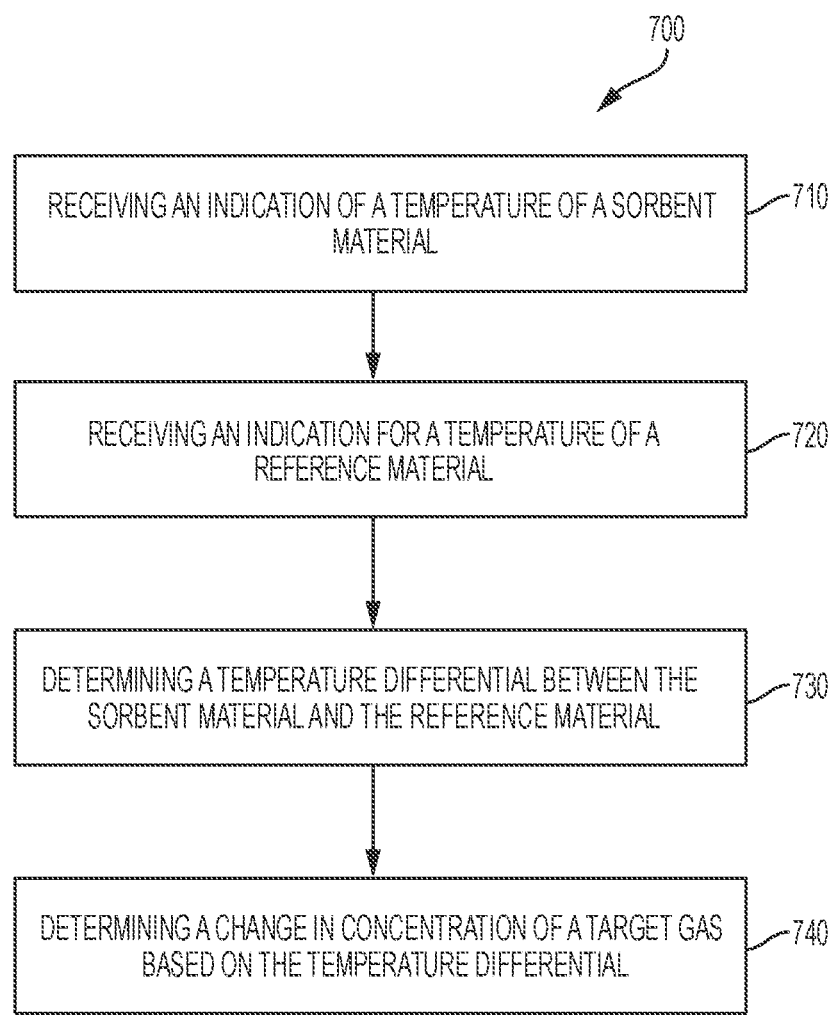
FIG. 7 is a flow diagram depicting a method of determining concentration of a target gas based on the temperature of a sorbent material, in accordance with some embodiments.

FIG. 7 is a flow diagram depicting a method 700 of determining concentration of a target gas from a differential temperature reading, according to an embodiment. In some embodiments, the method 700 may be performed by a gas monitor 100 as described with reference to FIG. 1. For example, the processing device 130 in FIG. 1 may perform the processes described with respect to method 700.

Beginning in block 710, a gas monitor may receive an indication of a temperature of a sorbent material exposed to a target gas in the environment. For example, the indication of the temperature of the sorbent material may be generated by providing a probe current to a thermistor coupled to the sorbent material. The voltage measured across the thermistor may provide an indication of the temperature of the sorbent material.

In block 720, a gas monitor may receive an indication of a temperature of a reference material. For example, the indication of the temperature of the reference material may be generated by providing a probe current to a thermistor coupled to the reference material. The voltage measured across the thermistor may provide an indication of the temperature of the reference material. The reference material may have physical and thermal properties similar to those of the sorbent material. For example, the reference material may change temperature in a similar manner in response to changed temperature in the environment. However, the reference material may be selected to not respond to the target gas or other gasses likely to be in the monitored environment. In some embodiments, the reference material may be the same as the sorbent material, but may have an encapsulation layer to prevent chemical interaction with the environment. Therefore, the layer may be thin enough to be thermally transparent, but prevent response to a target gas.

Moving on to block 730, the gas monitor may determine a differential between the sorbent material and the reference material. In some embodiments, the gas monitor may convert the indications of temperature received from the thermistors to corresponding temperature values. In some embodiments, the differential may be a difference between voltages received from the thermistors and may not be converted to corresponding temperatures. In some embodiments, the differential may be determined by providing a filter circuit to generate a signal representing the differential between the sorbent material and the reference material.

In block 740, the gas monitor may determine a change in concentration of a target gas based on the temperature differential. In some embodiments, the gas monitor may determine an amount of change in concentration based on the amount of different between the temperature readings. The gas monitor may also determine a length of time of the temperature differential to determine an absolute change in the concentration. For example, the gas monitor may integrate the differential to determine the absolute change in the concentration over a length of time.

Figure 8:
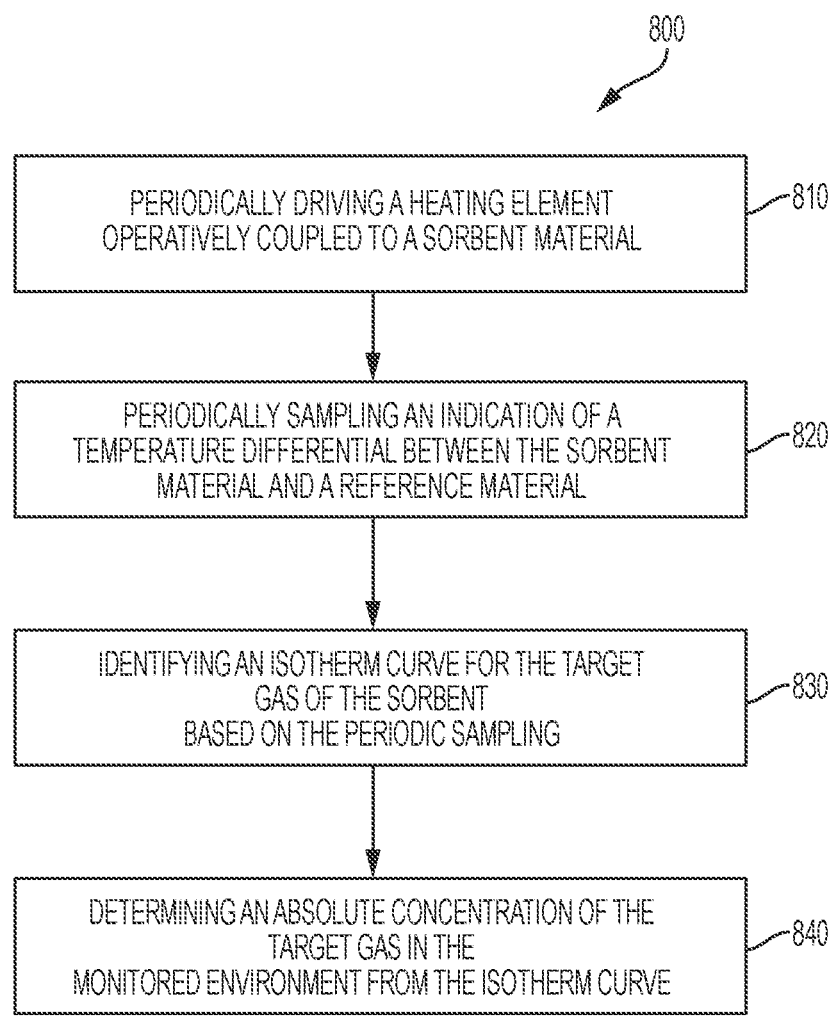
FIG. 8 is a flow diagram depicting a method of determining concentration of a target gas based on the temperature of a sorbent material, in accordance with some embodiments.

FIG. 8 is a flow diagram depicting a method 800 of determining concentration of a target gas from a differential temperature reading, according to an embodiment. In some embodiments, the method 800 may be performed by a gas monitor 200 as described with reference to FIG. 2. For example, the processing device 230 in FIG. 2 may perform the processes described with respect to method 800.

Beginning in block 810, a gas monitor may periodically drive a heating element operatively coupled to a sorbent material. In some embodiments, the heating element may be a resistive heating element that is driven by current provided by a processing device. The heating element may be driven with a sinusoidal waveform, a square waveform, or another waveform. In some embodiments, the heating element may be pulsed with a driving current to raise and lower the temperature. In some embodiments, the period of driving the heating element may be on a scale of about 0.1 Hz to about 100 Hz. In some embodiments, other driving signals may be provided to the heating element. In some embodiments, the heating element may also be coupled to a reference material or the gas monitor may also periodically drive a heating element associated with a reference material.

In block 820, the gas monitor may periodically sample an indication of a temperature differential between a sorbent material and a reference material. In some embodiments, the indication of the temperature differential of the sorbent material and the reference material may be provided by thermistors coupled to the sorbent material and the reference material. In some embodiments, the temperature differential may be sampled at a higher rate than the heating element is driven to provide data about the change in temperature at different points in the driving cycle.

In block 830, the gas monitor may identify an isotherm curve for the target gas of the sorbent material based on the periodic sampling of the temperature differential. For example, as discussed with reference to FIG. 6, multiple isotherm curves show how the amount of $CO_2$ on the sorbent material relates to the temperature of the material at different $CO_2$ concentrations in the monitored environment. The reference material would not change the relationship of its temperature in response to the heating element. Accordingly, by changing the temperature of the sorbent material by driving the heating element and measuring the temperature change between the sorbent material and the reference material, the gas monitor may determine an absolute concentration of $CO_2$ in the monitored environment. For example, the gas monitor may use a lookup table or array of data to determine an isotherm curve from the temperature differential. Other target gasses that are monitored using other sorbents may have similar isotherm curves that can be used in a similar monitor by the gas monitor.

In block 840, the gas monitor determines an absolute concentration of the target gas in the monitored environment from the isotherm curve. For example, after the isotherm curve is determined by comparing the temperature of the sorbent material to the temperature of the reference material, the gas monitor may determine a corresponding absolute concentration of the target gas from the curve. In some embodiments, the gas monitor may then provide the concentration to another system, provide an alert or alarm if certain conditions are met, or otherwise use the data to track the concentration of the target gas in the monitored environment.

Figure 9:
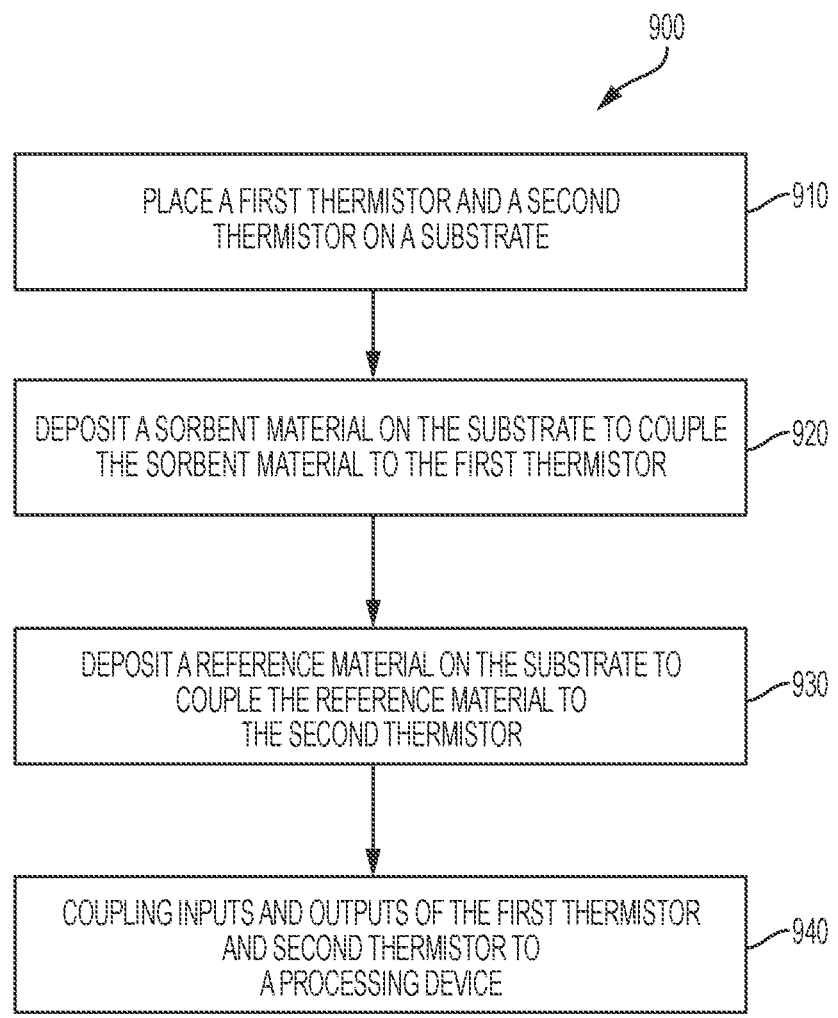
FIG. 9 is a flow diagram depicting a method of manufacturing a gas monitor, in accordance with some embodiments.

FIG. 9 is a flow diagram depicting a method 900 of manufacturing a gas monitor, according to an embodiment. For example, the method 900 shown in FIG. 9 may be used to manufacture the gas monitors 100, 200 described with reference to FIGS. 1 and 2. Beginning in block 910, a first thermistor and a second thermistor are operatively coupled to a substrate. In some embodiments, the first and second thermistor may be coupled in a position, such as a cavity, in the substrate that is prepared for the thermistors. For example, the substrate may have been etched to provide a receiving area for the thermistors. In some embodiments, the thermistors may be formed on the substrate with a printing process, may be soldered to the substrate, or may otherwise be coupled to the substrate.

In block 920, a sorbent material is deposited on the substrate coupled to the first thermistor. In some embodiments, the sorbent material may be combined with a binder and a solvent and printed in a manner to be operatively coupled to the first thermistor. Accordingly, the first thermistor may provide an accurate indication of the temperature of the sorbent material. In some embodiments, the sorbent material may be formed from a powder or other structure rather than a printed structure.

In block 930, a reference material is deposited on the substrate coupled to the second thermistor. In some embodiments, the reference material may be a selected such that it does not adsorb the target gas. The reference material may be combined with a binder and a solvent and printed in a manner to be operatively coupled to the second thermistor. Accordingly, the second thermistor may provide an accurate indication of the temperature of the reference material. In some embodiments, the reference material and the sorbent material are printed using the same or similar binders and solvents to improve consistency of the temperature change due to ambient temperature in the environment or heating elements. In some embodiments, the reference material may be formed from a powder or other structure rather than a printed structure.

In block 940, the thermistors may be coupled to a processing device. For example, the processing device may be one of processing device 130, 230 discussed with respect to FIG. 1. In some embodiments, the thermistors may be coupled to the processing device using traces on the surface of the substrate. In some embodiments, the processing device may be coupled to the thermistors using one or more leads separate from the substrate. The processing device may then drive and receive signals from the thermistors to determine the concentration of a target gas in a monitored environment.

Figure 10:
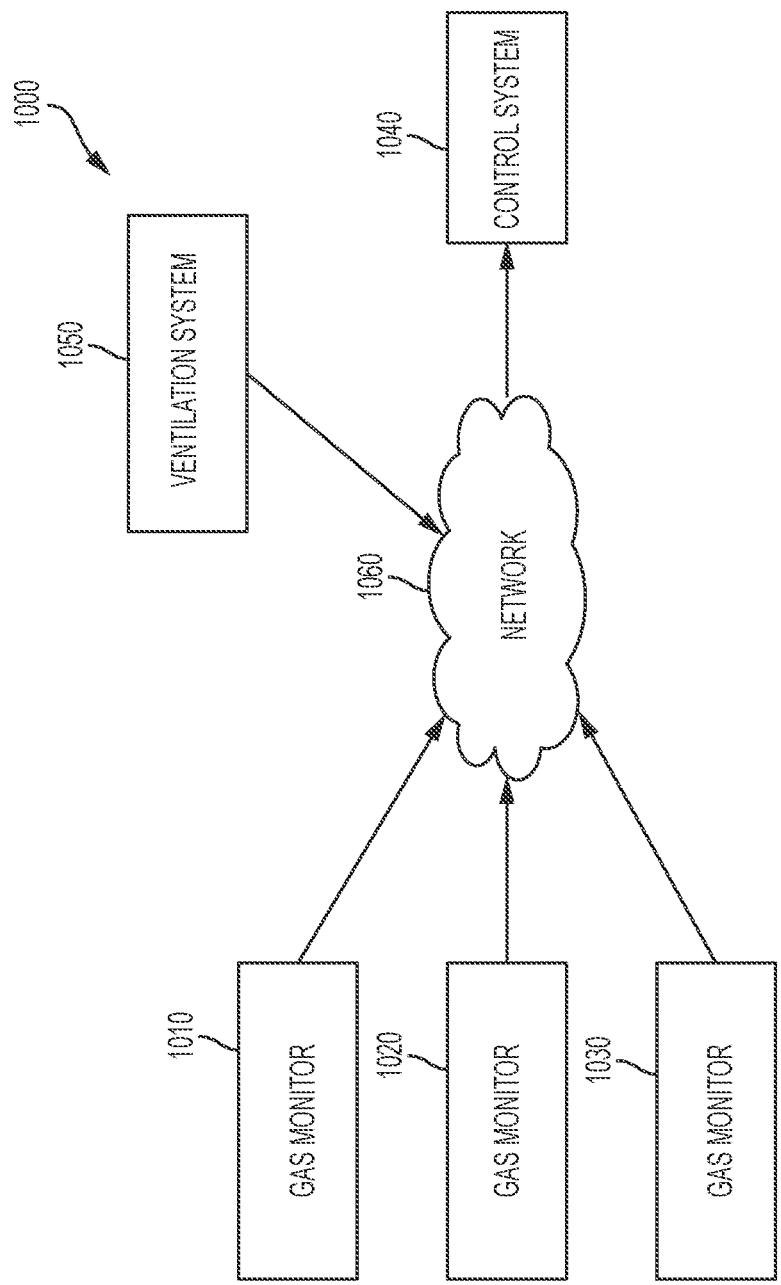
FIG. 10 is a schematic diagram of an embodiment of gas monitoring system, which can be used in accordance with some embodiments.

FIG. 10 a diagram showing an example embodiment of a gas monitoring system 1000. In some embodiments, the gas monitoring system 1000 includes a control system 1040, a ventilation system 1050, and a number of gas monitors 1010, 1020, 1030. For example, the gas monitors 1010, 1020, 1030 may be similar to those described with reference to FIGS. 1 and 2. In some embodiments, there may be fewer or additional gas monitors 1010, 1020, 1030 than shown in FIG. 10. Gas monitors 1010, 1020, 1030 may each measure concentration of one or more gasses. In some embodiments, the gas monitors 1010, 1020, 1030 monitor the same gas or gasses. For example, each of the gas monitors 1010, 1020, 1030 may monitor $CO_2$ at different locations within a facility. In some embodiments, gas monitors 1010, 1020, 1030 may measure the concentration of different gasses.

In some embodiments, the gas monitors 1010, 1020, 1030 may communicate with a control system 1040 over a network 1060. For example, the network may be a wired or wireless network including one of a local area network, an intranet, an extranet, the Internet, or another network. The control system 1040 may receive indications of temperature of sorbent and reference materials from the gas sensors and determine a concentration of target gasses for each gas monitor 1010, 1020, 1030 based on those indications. In some embodiments, the gas monitors 1010, 1020, 1030 transmit indications or measurements of the concentration of gas at the gas monitors 1010, 1020, 1030. Additionally, the gas monitors 1010, 1020, 1030 may transmit alerts or alarms based on one or more thresholds regarding the concentration of gasses at the gas monitors 1010, 1020, 1030.

In some embodiments, the control system 1040 may log data received from the gas monitors 1010, 1020, 1030. The control system 1040 may also determine one or more actions to take based on the data received from the gas monitors 1010, 1020, 1030. For example, if one or more of the gas monitors 1010, 1020, 1030 provide data indicating a gas concentration above or below a threshold level, the control system 1040 may activate one or more other systems to respond to the change. As an example, if the control system 1040 determines that a concentration of $CO_2$ indicated by one or more of the gas monitors 1010, 1020, 1030 is nearing or above a threshold level, the control system 1040 may provide commands to a ventilation system 1050 to increase the level of ventilation. In some embodiments, the control system 1040 may be coupled to additional systems to address additional gas concentrations. For example, if particular gas concentrations are detected, the control system 1040 may activate systems to decontaminate one or more rooms, monitor one or more rooms, or otherwise address potential adverse consequences due to the concentration of gas in a facility.

Although described with respect to gas monitoring of a facility, in some embodiments, the gas monitoring system 1000 may be deployed in other environments. For example, the gas monitoring system 1000 may be deployed in a car to manage interior air quality, in outdoor venues, or in other applications to monitor and log or respond to the concentration levels of one or more target gasses.

Various operations are described as multiple discrete operations, in turn, in a manner that is most helpful in understanding the present disclosure, however, the order of description may not be construed to imply that these operations are necessarily order dependent. In particular, these operations need not be performed in the order of presentation.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A gas monitor comprising:
   a sorbent material that selectively adsorbs a target gas based on a concentration of the target gas in a monitored environment, wherein the sorbent material is configured to passively absorb the target gas without heat being provided to the sorbent material;
   a reference material that comprises a same material as the sorbent material, wherein the reference material is encapsulated such that the reference material is not responsive to the target gas;
   a first thermistor disposed within the sorbent material and a second thermistor disposed within the reference material, the first thermistor to provide a first indication of a first temperature of the sorbent material and the second thermistor to provide a second indication of a second temperature of the reference material; and
   a processing device to determine a concentration of the target gas based at least in part on a differential measurement between the first temperature and the second temperature.

2. The gas monitor of claim 1, further comprising:
   a first heating element to provide heat to the sorbent material; and
   a second heating element to provide heat to the reference material, wherein the first heating element and the second heating element are to provide periodic heating to the sorbent material and the reference material to determine an absolute value of the concentration of the target gas or calibrate the gas monitor.

3. The gas monitor of claim 2, wherein the processing device is to determine the concentration of the target gas based on mapping the differential measurements to an isotherm curve for the target gas and sorbent.

4. The gas monitor of claim 1, wherein the sorbent material comprises a microporous or nano-porous carbon material and the target gas is carbon dioxide.

5. The gas monitor of claim 1, wherein the target gas is one of carbon dioxide, carbon monoxide, benzene, or Formaldehyde.

6. The gas monitor of claim 1, wherein the sorbent material comprises a printed sorbent ink with a binder.

7. The gas monitor of claim 1, further comprising a chamber allowing gas flow along the sorbent material and the reference material.

8. The gas monitor of claim 1, further comprising:
   a second sorbent material that selectively adsorbs a second target gas; and
   a third thermistor disposed within the second sorbent material, wherein the processing device is further to determine a concentration of the second target gas based at least in part on an output of the third thermistor.

9. A method comprising:
   receiving an indication of a first temperature of a sorbent, wherein the sorbent changes temperature based on a heat of adsorption of a target gas, wherein the sorbent is configured to passively absorb the target gas without heat being provided to the sorbent;
   determining a second temperature based on a second indication of the second temperature received from a thermistor coupled to a reference material, wherein the reference material comprises a same material as the sorbent that is encapsulated such that the reference material does not respond to the target gas; and
   determining, based at least in part on the indication of the first temperature of the sorbent and the second temperature of the reference material, a concentration of the target gas in a monitored environment in contact with the sorbent.

10. The method of claim 9, further comprising:
periodically driving a heating element operatively coupled to the sorbent, wherein determining the concentration of the sorbent comprises determining an absolute value of the concentration based on a difference in the indication of the first temperature of the sorbent relative to a third temperature due to the heating element.

11. The method of claim 10 further comprising comparing changes in the difference to an isotherm curve for the sorbent in the presence of the target gas.

12. The method of claim 10, wherein periodically driving the heating element comprising driving the heating element at a rate greater 0.1 Hz and less than 100 Hz.

13. The method of claim 9, wherein the target gas is one of carbon dioxide, carbon monoxide, benzene, or Formaldehyde.

14. A method comprising:
coupling a first thermistor and a second thermistor to a substrate;
depositing a sorbent material on the substrate to couple the sorbent material to the first thermistor, wherein the sorbent material selectively adsorbs a target gas based on a concentration of the target gas in a monitored environment, and wherein the sorbent material is configured to passively absorb the target gas without heat being provided to the sorbent material;
depositing a reference material on the substrate to couple the reference material to the second thermistor, wherein the reference material comprises a same material as the sorbent material that is encapsulated such that the reference material is not responsive to the target gas; and
coupling the first thermistor and the second thermistor to a processing device.

15. The method of claim 14, wherein the method further comprises:
providing a first heating element coupled to the sorbent material; and
providing a second heating element coupled to the reference material, wherein the first heating element and the second heating element are to provide periodic heating to the sorbent material and the reference material to determine an absolute value of the concentration of the target gas.

16. The method of claim 14, wherein depositing the sorbent material comprises printing the sorbent material mixed with at least one of a binder or a solvent.

17. The method of claim 14, wherein depositing the sorbent material further comprises depositing the sorbent material with a porous glassy solid binder.

18. The method of claim 14, wherein depositing the sorbent material further comprises depositing a sorbent ink comprising the sorbent material, a styrene acrylic-based polymer latex, and a solvent.

* * * * *